US00PP37817P2

(12) United States Plant Patent
Masor

(10) Patent No.: US PP37,817 P2
(45) Date of Patent: Oct. 20, 2026

(54) CALIBRACHOA PLANT NAMED 'BALUMINK617'

(50) Latin Name: ***Calibrachoa* x *hybrida***
Varietal Denomination: 'Balumink617'

(71) Applicant: Ball Horticultural Company, West Chicago, IL (US)

(72) Inventor: Laura Masor, Buda, TX (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 19/349,979

(22) Filed: Oct. 4, 2025

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./413
See application file for complete search history.

(56) References Cited

U.S. PATENT DOCUMENTS

PP36,624 P3 * 4/2025 Barnes ..... A01H 5/02
Plt./413

* cited by examiner

*Primary Examiner* — Susan Mccormick Ewoldt
*Assistant Examiner* — Zachariah Allan Kay
(74) *Attorney, Agent, or Firm* — Megan Bowman

(57) ABSTRACT

A new and distinct cultivar of *Calibrachoa* plant named 'Balumink617', characterized by its light pink-colored flowers having a yellow coloration forming a shallow star pattern, medium green-colored foliage, and moderately vigorous, mounded growth habit, is disclosed.

1 Drawing Sheet

Latin name of genus and species of plant claimed: *Calibrachoa* x *hybrida*.

Variety denomination: 'Balumink617'.

BACKGROUND OF THE INVENTION

The present invention relates to a new and distinct cultivar of *Calibrachoa* plant botanically known as *Calibrachoa* x *hybrida* and hereinafter referred to by the cultivar name 'Balumink617'.

The new cultivar originated in a controlled breeding program in Arroyo Grande, California during June 2021. The objective of the breeding program was the development of *Calibrachoa* cultivars with bright, vibrant novelty flower coloration, and a moderately vigorous, mounded growth habit.

The new *Calibrachoa* cultivar is the result of cross-pollination. The female (seed) parent is BUMBLE BEE Hot Pink, 'Balumotink', U.S. Plant Pat. No. 33,305, characterized by its deep, pink-colored flowers having a yellow coloration forming a shallow, central star pattern, medium, green-colored foliage, and moderate, mounded-trailing growth habit. The male (pollen) parent of the new cultivar is BUMBLE BEE Orange, 'Balbumorim', not patented, characterized by its orange flowers having a yellow star pattern and mottled, red-colored overlay, medium, green-colored foliage, and moderate, mounded growth habit. The new cultivar was selected as a single flowering plant within the progeny of the above stated cross-pollination during March 2022 in a controlled environment in Arroyo Grande, California.

Asexual reproduction of the new cultivar by terminal stem cuttings since March 2022 in Arroyo Grande, California and West Chicago, Illinois has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'Balumink617' as a new and distinct cultivar of *Calibrachoa* plant:

1. Light, pink-colored flowers having a yellow coloration forming a shallow, central star pattern;
2. Medium, green-colored foliage; and
3. Moderately vigorous, mounded growth habit.

Plants of the new cultivar differ from plants of the female and male parents primarily in having a light pink flower color.

Of the many commercially available *Calibrachoa* cultivars, the most similar in comparison to the new cultivar is SUPERBELLS Pink, 'WNCALSBPK24', U.S. Plant Pat. No. 36,624. However, in side-by-side comparisons, plants of the new cultivar differ from plants of 'Balumink617' in at least the following characteristics:

Plants of the new cultivar have petals with bright yellow midveins forming a star, unlike plants of 'WNCALSBPK24';

Plants of the new cultivar have branches with longer internodes than plants of 'WNCALSBPK24'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balumink617'. The approximately 5-month-old plants were grown in 4.5-inch pots in a double polyethylene greenhouse in West Chicago, Illinois. Plants were given one pinch two weeks before transplant.

DETAILED BOTANICAL DESCRIPTION

Figure 1:
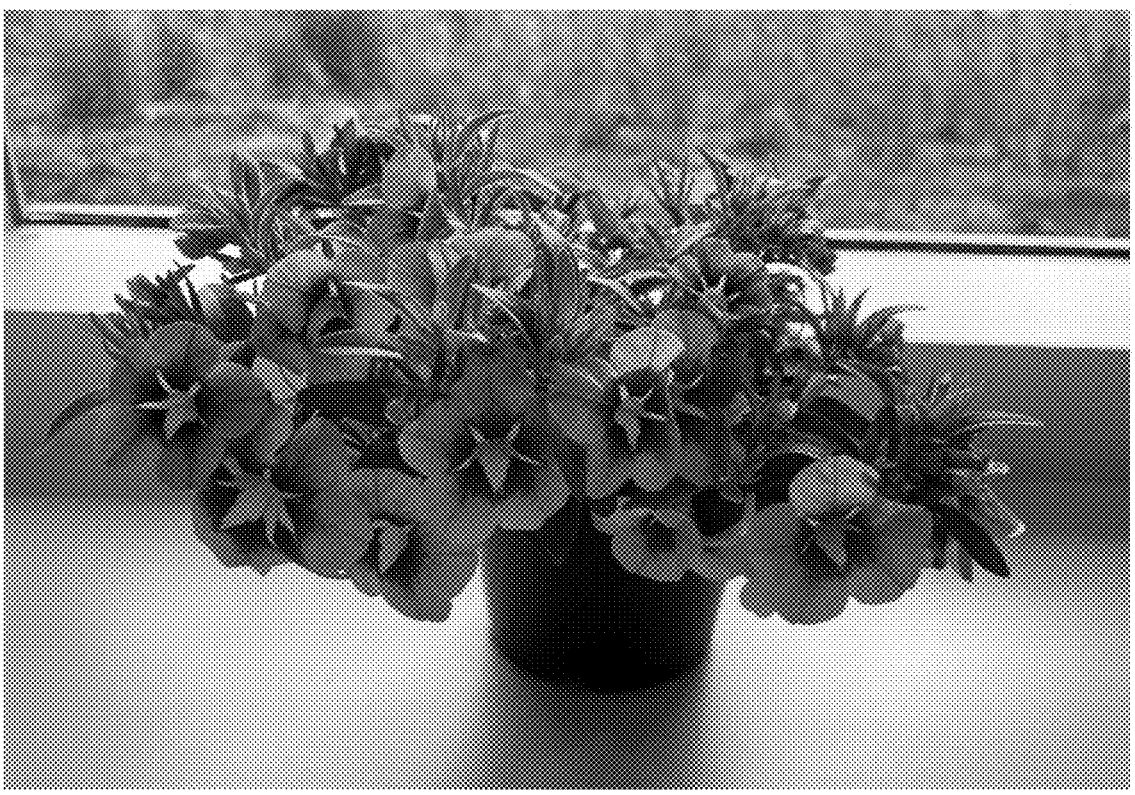
FIG. 1 illustrates a side view of the overall growth and flowering habit of 'Balumink617'.
Figure 2:
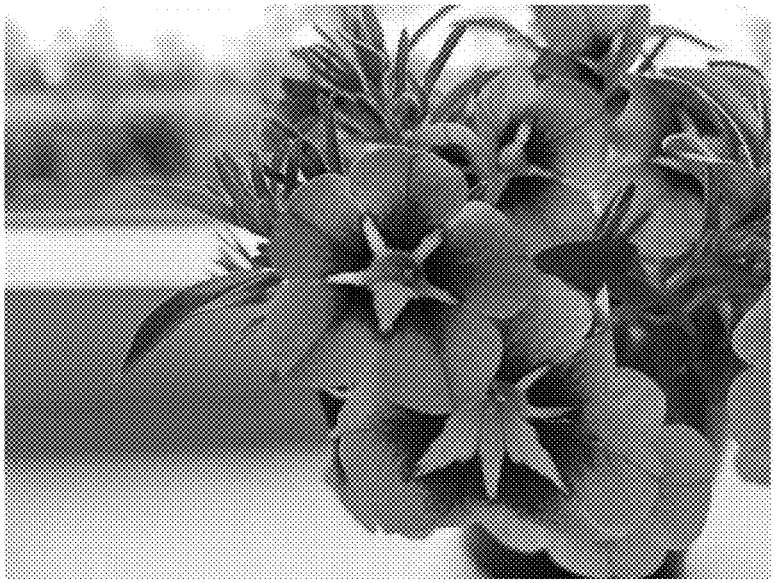
FIG. 2 illustrates a close-up view of an individual flower of 'Balumink617'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in April 2025 under natural light conditions in West Chicago, Illinois.

The following descriptions and measurements describe approximately 5-month-old plants produced from cuttings from stock plants and grown in a double polyethylene greenhouse under conditions comparable to those used in commercial practice. The plants were grown in West Chicago, Illinois in 4.5-inch pots for 6 weeks utilizing a soilless growth medium. Plants were given one pinch three weeks before transplant. After approximately six weeks, plants were then transplanted and grown for approximately 14 weeks. Greenhouse temperatures were maintained at approximately 65° F. to 70° F. (18.3° C. to 21.1° C.) during the day and approximately 60° F. to 65° F. (15.6° C. to 18.3° C.) during the night. Supplemental lighting was used. Measurements and numerical values represent averages of typical plants.

Botanical classification: *Calibrachoa* x *hybrida* 'Balumink617'.

Parentage:

*Female parent*.—BUMBLE BEE Hot Pink, 'Balumotink', U.S. Plant Pat. No. 33,305.

*Male parent*.—BUMBLE BEE Orange, 'Balbumorim', not patented.

Propagation:

*Type cutting*.—Terminal stem.

*Time to initiate roots*.—Approximately 6 to 8 days.

*Time to produce a rooted cutting*.—Approximately 21 to 28 days.

*Root description*.—Fibrous.

*Rooting habit*.—Freely branching.

Plant description:

*Commercial crop time*.—Approximately 6 to 9 weeks from a rooted cutting to finish in a 10 cm pot.

*Growth habit and general appearance*.—Moderately vigorous, mounded.

*Size*.—Height from soil level to top of plant plane: Approximately 8.0 cm. Width: Approximately 25.5 cm.

*Branching habit*.—Freely branching, pinching enhances basal branching. Quantity of main branches per plant: Approximately 4.

*Branch*.—Strength: Moderate. Length: Approximately 10.0 cm. Diameter: Approximately 2.0 mm. Length of central internode: Approximately 1.5 cm. Texture: Densely pubescent. Color of young stems: 144B. Color of mature stems: 146A with a slight overlay of 79A.

Foliage description:

*General description*.—Fragrance: None detected. Form: Simple. Arrangement on flowering stem: Opposite.

*Leaves*.—Aspect: At acute angle to stem with tip turning downward. Shape: Elliptic. Margin: Entire. Apex: Broadly acute. Base: Attenuate. Venation pattern: Pinnate. Length of mature leaf: Approximately 4.0 cm. Width of mature leaf: Approximately 1.5 cm. Texture of upper and lower surfaces: Moderately glandular pubescent. Gland color: Colorless, transparent. Color of upper surface of young and mature foliage: 137A with midvein of 146C. Color of lower surface of young and mature foliage: Closest to 138A with midvein of 146D.

*Petiole*.—Length: Approximately 3.0 mm. Diameter: Approximately 1.0 mm. Texture: Moderately glandular pubescent. Gland color: Colorless, transparent. Color: N144B.

Flowering description:

*Flowering habit*.—'Balumink617' is freely flowering under outdoor growing conditions with substantially continuous blooming from spring through autumn and year-round in greenhouse environment.

*Lastingness of individual flower on the plant*.—Approximately 5 to 7 days.

Flower description:

*General description*.—Type: Single, salverform. Quantity per plant: Approximately 25. Fragrance: None detected.

*Bud*.—Rate of opening: Generally, takes 3 to 4 days for bud to progress from first color to fully open flower. Quantity per plant: Approximately 10.

*Bud just before opening*.—Shape: Oblong. Length: Approximately 2.5 cm. Diameter: Approximately 5.0 mm. Texture: Densely glandular pubescent. Gland color: Colorless, transparent. Color: Petal portion 63C, tube portion 154B, venation of N79B.

*Corolla*.—Diameter: Approximately 4.0 cm.

*Petals*.—Quantity: 5, fused to form a tube. Shape: Obovate. Margin: Entire. Apex: Obtuse, occasionally shallowly notched. Length from tube: Approximately 1.5 cm. Length of free portion: Approximately 8.0 mm. Width: Approximately 1.7 cm. Texture of upper surface: Glabrous. Texture of lower surface: Glandular pubescent, dense along venation. Gland color: Colorless, transparent. Color of upper surface when first open: Between N74B and NN78A with midveins of N79C and 3A forming a star pattern. Color of lower surface when first and fully open: 68B with midveins of N79A. Color of upper surface when fully open: Between N66D and N74B and midveins of NN74A and 7A forming a star pattern. Color of lower surface when fully open: 63D with midveins of N79C.

*Corolla tube*.—Length: Approximately 2.0 cm. Diameter at distal end: Approximately 5.0 mm. Diameter at proximal end: Approximately 1.0 mm. Texture of inner surface: Glabrous. Texture of outer surface:

Densely glandular pubescent. Gland color: Colorless, transparent. Color of inner surface: 3A, venation of 144C. Color of outer surface: 2B with venation of 59A.

*Sepals*.—Quantity per flower: 5, fused at base. Shape: Lanceolate. Apex: Acute. Length: Approximately 1.6 to 1.8 cm. Width: Approximately 2.0 mm. Texture of upper and lower surfaces: Densely glandular pubescent. Gland color: Colorless, transparent. Color of upper surface: 143A. Color of lower surface: 143B with base of 144D.

*Peduncle*.—Strength: Strong, flexible. Aspect: Acute angle to stem. Length: Approximately 1.1 cm. Diameter: Approximately 1.0 mm. Texture: Densely glandular pubescent. Gland color: Colorless, transparent. Color: N144A.

*Reproductive organs*.—Androecium: Stamen quantity: 5, basifixed. Stamen length: Approximately 0.8 cm. Filament length of fixed portion: Approximately 4.0 mm. Filament color: 150D. Anther shape: Bilobed, ovoid. Anther length: Approximately 1.0 mm. Anther color: 17B. Pollen amount: Abundant. Pollen color: 8C. Gynoecium: Pistil quantity: 1 per flower. Pistil length: Approximately 8.0 mm. Stigma shape: Funnel. Stigma length: Less than 1.0 mm. Stigma color: 145A. Style length: Approximately 7.0 mm. Style color: 145A. Ovary diameter: Approximately 2.0 mm. Ovary color: 144B.

Seed and fruit production: Neither seed nor fruit production has been observed.

Disease and pest resistance: Resistance to pathogens and pests common to *Calibrachoa* has not been observed.

What is claimed is:

1. A new and distinct cultivar of *Calibrachoa* plant named 'Balumink617', substantially as herein illustrated and described.

* * * * *